US008435732B2

(12) United States Patent
Chattopadhyay et al.

(10) Patent No.: US 8,435,732 B2
(45) Date of Patent: May 7, 2013

(54) CHIMERIC CONSTRUCT OF MUNGBEAN YELLOW MOSAIC INDIA VIRUS (MYMIV) AND ITS USES THEREOF

(75) Inventors: Debasis Chattopadhyay, New Delhi (IN); Rajiv Kumar Yadav, New Delhi (IN); Rakesh Kumar Shukla, New Delhi (IN)

(73) Assignee: National Institute for Plant Genome Research (IN)

( * ) Notice: Subject to any disclaimer, the term of this patent is extended or adjusted under 35 U.S.C. 154(b) by 185 days.

(21) Appl. No.: 12/746,429

(22) PCT Filed: Dec. 8, 2008

(86) PCT No.: PCT/IN2008/000819

§ 371 (c)(1), (2), (4) Date: Jun. 4, 2010

(87) PCT Pub. No.: WO2009/072147

PCT Pub. Date: Jun. 11, 2009

(65) Prior Publication Data

US 2010/0285445 A1 Nov. 11, 2010

(30) Foreign Application Priority Data

Dec. 7, 2007 (IN) ........................... 2571/DEL/2007

(51) Int. Cl.

| | |
|---|---|
| ***C12Q 1/70*** | (2006.01) |
| ***C12Q 1/02*** | (2006.01) |
| ***C12N 15/34*** | (2006.01) |
| ***C12N 15/84*** | (2006.01) |
| ***C12N 5/14*** | (2006.01) |
| ***C12N 1/21*** | (2006.01) |
| ***C07H 21/04*** | (2006.01) |

(52) U.S. Cl.

USPC .............. 435/5; 435/29; 435/320.1; 435/469; 435/419; 435/252.33; 435/252.2; 536/23.72; 536/24.33

(58) Field of Classification Search ........................ None
See application file for complete search history.

(56) References Cited

U.S. PATENT DOCUMENTS 4,789,636 A 12/1988 Morinaga

OTHER PUBLICATIONS

Genbank AY26992.1 (Mar. 20, 2004).*
Genbank AY939925 (Mar. 1, 2006).*
Hayes et al (Journal of General Virology 69:1487-1496, 1988).*
Buck et al (Biotechniques 27:528-536, 1999).*
Genbank AF142440 (Mar. 7, 2003).*
"AY049771—IMungbean yellow mosaic India virus-[Soybean] segment DNA B, complete sequence", *EMBL Database*, (Sep. 17, 2001).
"AY049772—Mungbean yellow mosaic India virus-[Soybean] segment DNA A, complete sequence", *EMBL Database*, (Sep. 17, 2001).
"AY939925—Mungbean yellow mosaic India virus segment B, complete sequence", *EMBL Database*, (Mar. 2, 2006).
"DQ389153—Mungbean yellow mosaic India virus segment DNA A, complete sequence", *EMBL Database*, (May 3, 2006).
"DQ400847—Mungbean yellow mosaic India virus segment DNA A, complete sequence", *EMBL Database*, (Mar. 14, 2006).
"International Application Serial No. PCT/IN2008/000819, International Search Report", (Mar. 16, 2009), 5 pgs.
Ferreira, P., et al., "One-step cloning approach for construction of agroinfectious begomovirus clones", *Journal of Virological Methods*, 147(2), (Feb. 2008), 351-354.
Girish, K. R, et al., "Molecular characterization of two soybean-infecting begomoviruses from India and evidence for recombination among legume-infecting begomoviruses from South [corrected] South-East Asia.", *Virus Res*., 108(1-2), (Mar. 2005), 167-76.
Grimsley, N., et al., ""Agroinfection," an alternative route for viral infection of plants by using the Ti plasmid.", *Proc Natl Acad Sci* U S A., 83(10), (May 1986), 3282-3286.
Jacob, S. S, et al., "Mungbean yellow mosaic virus-Vi Agroinfection by Codelivery of DNA A and DNA B From One *Agrobacterium* Strain", *Plant Disease*, 87(3), (Mar. 2003), 247-251.
Rouhibakhsh, A., et al., "An improved DNA isolation method and PCR protocol for efficient detection of multicomponents of begomovirus in legumes", *J Virol Methods*, 147(1), (Jan. 2008), 37-42.
Usharani, K., et al., "Infectivity analysis of a soybean isolate of Mungbean yellow mosaic India virus by agroinoculation", *Journal of General Plant Pathology*, 71(3), (Jun. 2005), 230-237.

* cited by examiner

*Primary Examiner* — Mary E Mosher
(74) *Attorney, Agent, or Firm* — Schwegman Lundberg & Woessner, P.A.

(57) ABSTRACT

A recombinant DNA construct, recombinant vectors and host cells comprising the dimers of DNA A and DNA B of Mungbean Yellow Mosaic India Virus (MYMIV) in a single Ti plasmid are provided herein.

9 Claims, 4 Drawing Sheets

CHIMERIC CONSTRUCT OF MUNGBEAN YELLOW MOSAIC INDIA VIRUS (MYMIV) AND ITS USES THEREOF

This application is a U.S. National Stage Filing under 35 U.S.C. 371 from International Patent Application Serial No. PCT/IN2008/000819, filed Dec. 8, 2008, and published on Jun. 11, 2009 as WO 2009/072147 A1, which claims the priority benefit of Indian Application No. 2571/DEL/2007, filed Dec. 7, 2007, the contents of which are incorporated herein by reference in their entirety.

FIELD OF INVENTION

The present invention relates to the field of molecular biology. More specifically the present invention pertains to construction of a virulent clone of Mungbean Yellow Mosaic India Virus (MYMIV) and its uses thereof.

BACKGROUND OF THE INVENTION

Mungbean yellow mosaic disease is characterized by a bright yellow mosaic on the leaves of infected plants and causes significant losses to mungbean (*Vigna radiata*) crops. Yellow Mosaic Disease is a major threat for five important pulse crops Black gram, Mungbean, French bean, Pigeon pea and Soybean. It causes an annual loss of about $300 million. Soybean is one of the major pulse crops. It is highly prone to yellow mosaic disease and causes yield loss of 21-86% depending on severity. The causative agent of this disease is identified as Mungbean Yellow Mosaic India Virus (MYMIV), which is a member of Geminivirus group and Begomovirus family. The virus in India is transmitted through whitefly. Symptoms of the disease include small yellow diffused patches, which coalesce making the leaf completely yellow. Newer leaves show, yellow mosaic and mottling.

MYMIV, like most of the bipartite Geminivirus, contain two single stranded, covalently closed circular DNA as their genetic material. These are named as DNA-A and DNA-B, each of approximately 2.7 kb in size. DNA A encodes mainly 4 proteins, which play important role in replication and transcription of both the DNA components. DNA B encodes only two proteins, which help in the movement of the viral particles. They replicate through double stranded DNA intermediates in nuclei of mature plant cells.

To study many biological processes of these bipartite Begomoviruses, and to screen resistant variety in a population, plants need to be infected with the virus. For this purpose many infection methods have been developed such as (1) Virus transmission from an infected plant to uninfected plant with the help of whitefly (*B. tabaci*) (2) Mechanical inoculation of purified virus or viral DNA dimers from infected plant to healthy plant and (3) Inoculation of *Agrobacterium* suspension having partial or full dimers of DNA A and DNA B in Ti plasmid.

The whitefly mediated inoculation is the oldest method used for infecting plant. But some of the important bipartite Begomovirus are non transmissible to the other hosts by white flies and frequency of infection is low as it depends upon whitefly. Further, maintaining the stock of pure virus-containing whiteflies is very inconvenient and hazardous; and completely controlled introduction of insects to the plant is difficult. Screening of seed population is also not fully reliable in whitefly mediated infection; as the resistance may arise against whitefly itself (Grimsley, N., Hohn, B., Hohn, T., and Walden, R. (1986). "Agroinfection", an alternative route for viral infection of plants by using the Ti plasmid. Proc. Natl. Acad. Sci. USA 83:3282-3286).

To overcome the difficulties of using insect vector for viral inoculations, mechanical methods were also tested in early studies. These methods involve inoculation of purified virus or dimers of DNA A and B to an uninfected plant via mechanical injuries (Etessami, P., Callis, R., Ellwood, S., Stanley, J., (1988). Delimitation of essential genes of cassava latent virus DNA 2. Nucleic Acid Res. 16, 4811-4829). In few plants such as Tomato 100% infection were obtained by using these methods. But results were not so promising. Other viruses like maize streak virus, beet curly top virus and squash leaf curl virus which are not transmitted mechanically an efficient method for infection is needed (Stanley, J., Markham, P. G., Callis, R. J., Pinner, M. S., (1986). The nucleotide sequence of an infectious clone of the geminivirus beet curly top virus. EMBO J. 5, 1761-1767).

Since most of the geminiviruses are not mechanically transmissible so new approaches such as *Agrobacterium* mediated inoculation was found to be reliable and suitable method for artificial infection of plants with these viruses (Grimsley, N., Hohn, B., Hohn, T., and Walden, R. (1986) "Agroinfection", an alternative route for viral infection of plants by using the Ti plasmid. Proc. Natl. Acad. Sci. USA. 83:3282-3286). Using this method Petunia plants were inoculated with Tomato Golden Mosaic Virus (Rogers, S. G., Bisaro, D. M., Horsch, R. B., Fraley, R. T., Hoffmann, N. L., Brand, L., Elmer, J. S., and Lloyd, A. M. (1986) Tomato golden mosaic virus A component DNA replicates autonomously in transgenic plants. Cell 45:593-600). It was the first report of Agroinoculation of a Bipartite Begomovirus. This method uses the ability of *Agrobacterium* to transfer its Ti plasmid DNA from bacterial cell to plant chromosome by recombination (Wang, K; Herrera-Estrella, L; Van Montagu, M; Zambryski, P. Right 25 bp terminus sequence of the nopaline T-DNA is essential for and determines direction of DNA transfer from *agrobacterium* to the plant genome. Cell. (1984) September; 38(2):455-462).

Generally for infecting the plants with the MYMIV, partial dimers or full dimers of DNA A and DNA B of a bipartite Begomovirus is cloned into T-DNA of two separate Ti plasmids and introduced into separate *Agrobacterium* culture. These two *Agrobacterium* cultures, having dimer of DNA A and dimer of DNA B are mixed in equal amount and used for plant inoculation called as co-Agroinoculation. After recombination and transfer of T-DNA to the plant chromosomes, unit-length Geminivirus genomes are released with the help of virus and plant proteins. This method is widely used for many Begomoviruses like Tomato Golden Mosaic Virus, Mungbean yellow mosaic virus Mungbean, Yellow Mosaic India Virus (Katoor S. Usharani, Baliji Surendranath, Qazi M. R. Haq and Varagur G. Malathi (2005), Infectivity analysis of a soybean isolate of Mungbean yellow mosaic India virus by agroinoculation. J Gen Plant Pathol 71:230-237) and Potato yellow mosaic virus and Cassava mosaic virus.

In a modified version of Agroinoculation method of bipartite Begomovirus, DNA A and DNA B partial tandem repeats were cloned on two separate Ti plasmids DNAs and introduced into same *Agrobacterium* cell and used for plant inoculation (Jacob S S, Vanitharani R, Karthikeyan A S, Chinchore Y, Thillaichidambaram P and Veluthambi K (2003) Mungbean yellow mosaic virus-Vi agroinfection by codelivery of DNA A and DNA B from one *Agrobacterium* strain; Plant Dis. 87 247-251).

Recent study of the infection of MYMIV on Soybean plant was carried out by inoculating the plant with mixed *Agrobacterium* cultures harboring separately partial dimers of DNA A and DNA B. The maximum efficiency of infection was found only 21% (Katoor S. Usharani, Baliji Surendranath, Qazi M. R. Haq and Varagur G. Malathi (2005) Infectivity analysis of a soybean isolate of Mungbean yellow mosaic India virus by agroinoculation. J. Gen. Plant Pathol. 71:230-237). Therefore there is need for a better system for infecting the plants with Mungbean Yellow Mosaic India Virus (MYMIV) that gives higher efficiency of infection of plants with the virus.

BRIEF DESCRIPTION OF ACCOMPANYING DRAWINGS

Figure 3:
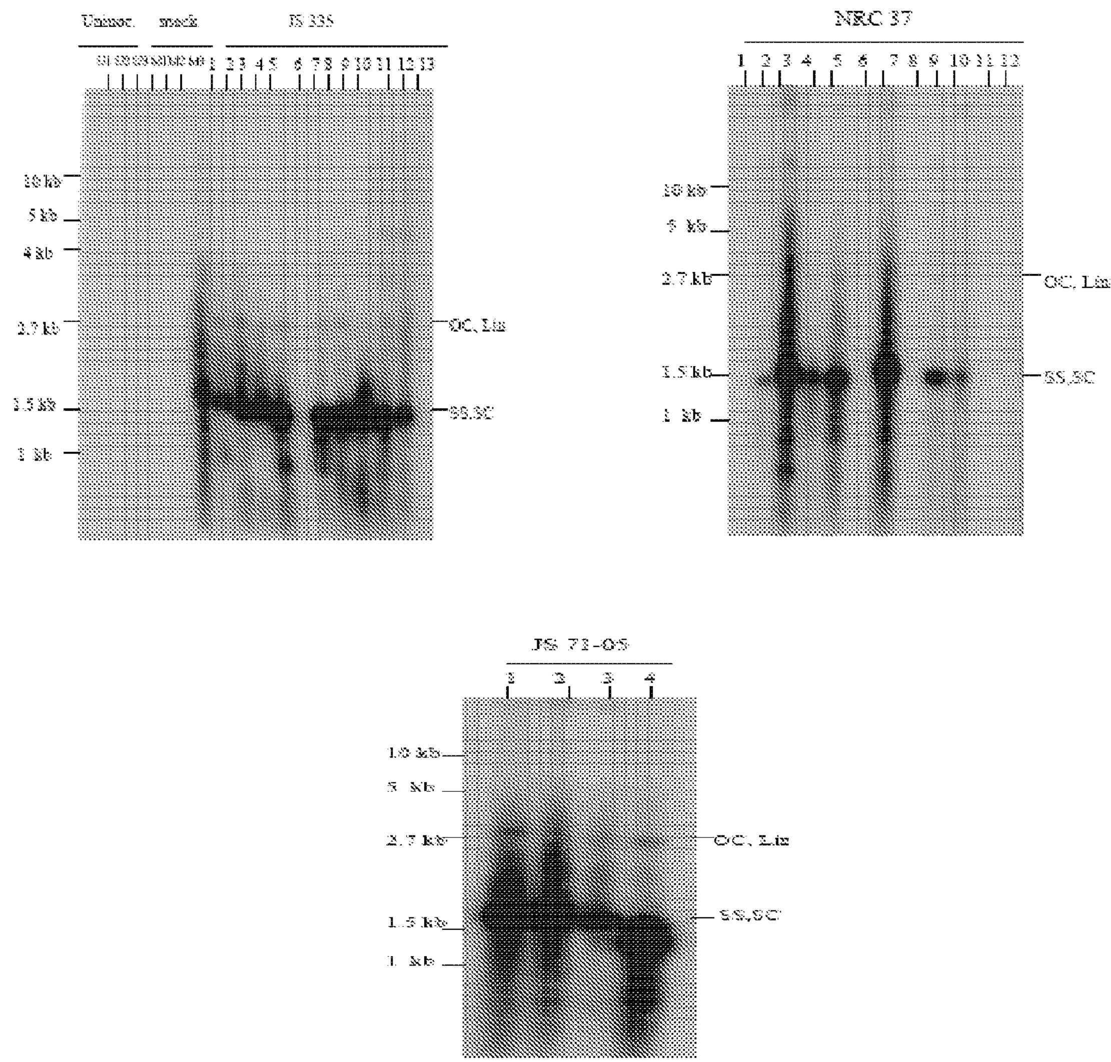

FIG. 3 shows southern blot analysis of total DNA extracted from soybean plants, agroinoculated with culture of *Agrobacterium* harboring pCAMBIAA2B2. Rep protein gene fragment of DNA-A was used as probe. Mock inoculated (M) and uninoculated (U) plants were also analyzed. OC=open circular, Lin=linear, SC=super coiled, SS=single stranded.

DETAILED DESCRIPTION OF THE INVENTION

The present invention relates to construction of a virulent clone of Mungbean Yellow Mosaic India Virus (MYMIV) and its uses thereof. The present invention provides a recombinant construct, recombinant vectors and host cells comprising the dimers of DNA A and DNA B of Mungbean Yellow Mosaic India Virus (MYMIV).

One embodiment of the present invention provides a recombinant DNA construct comprising dimers of MYMIV DNA A and DNA B of Mungbean Yellow Mosaic India Virus (MYMIV) in a single Ti plasmid.

Another embodiment of the present invention provides recombinant DNA construct comprising dimers of MYMIV DNA A and DNA B of Mungbean Yellow Mosaic India Virus (MYMIV) in a single Ti plasmid, wherein the polynucleotide sequence of DNA A is as set forth in SEQ ID NO: 11 or SEQ ID NO: 13 and the polynucleotide sequence of DNA B is as set forth in SEQ ID NO: 12 or SEQ ID NO: 14.

Yet another embodiment of the present invention provides a recombinant vector comprising dimers of MYMIV DNA A and DNA B of Mungbean Yellow Mosaic India Virus (MYMIV) in a single Ti plasmid.

Still yet another embodiment of the present invention provides recombinant vector comprising dimers of MYMIV DNA A and DNA B of Mungbean Yellow Mosaic India Virus (MYMIV) in a single Ti plasmid, wherein the polynucleotide sequence of DNA A is as set forth in SEQ ID NO: 11 or SEQ ID NO: 13 and the polynucleotide sequence of DNA B is as set forth in SEQ ID NO: 12 or SEQ ID NO: 14.

One of the embodiments of the present invention provides a recombinant vector comprising dimers of MYMIV DNA A of Mungbean Yellow Mosaic India Virus (MYMIV), wherein the polynucleotide sequence of the DNA A is as set forth in SEQ ID NO: 11 or SEQ ID NO:13.

Yet another embodiment of the present invention provides a recombinant vector comprising dimers of MYMIV DNA B of Mungbean Yellow Mosaic India Virus (MYMIV), wherein the polynucleotide sequence of the DNA B is as set forth in SEQ ID NO: 12 or SEQ ID NO: 14.

Yet another embodiment of the present invention provides the recombinant plant transformation vectors comprising dimers of MYMIV DNA A and DNA B of Mungbean Yellow Mosaic India Virus (MYMIV) in a single Ti plasmid, wherein the polynucleotide sequence of DNA A is as set forth in SEQ ID NO: 11 and the polynucleotide sequence of DNA B is as set forth in SEQ ID NO: 12.

Still yet another embodiment of the present invention provides the recombinant plant transformation vectors comprising dimers of MYMIV DNA A and DNA B of Mungbean Yellow Mosaic India. Virus (MYMIV) in a single Ti plasmid, wherein the polynucleotide sequence of DNA A is as set forth in SEQ ID NO: 13 and the polynucleotide sequence of DNA B is as set forth in SEQ ID NO: 14.

Further embodiment of the present invention provides the recombinant plant transformation vectors comprising dimers of MYMIV DNA A of Mungbean Yellow Mosaic India Virus (MYMIV), wherein the polynucleotide sequence of DNA A is as set forth in SEQ ID NO: 11.

Yet another embodiment of the present invention provides the recombinant plant transformation vector comprising dimers of DNA B of Mungbean Yellow Mosaic India Virus (MYMIV), wherein the polynucleotide sequence of DNA B is as set forth in SEQ ID NO: 12.

The present invention provides the recombinant host cell comprising dimers of MYMIV DNA A and DNA B of Mungbean Yellow Mosaic India Virus (MYMIV) in a single Ti plasmid, wherein the host cell is selected from a group consisting of *E. coli*, and *Agrobacterium.*

The present invention also provides the plant cell comprising dimers of MYMIV DNA A and DNA B of Mungbean Yellow Mosaic India Virus (MYMIV).

Yet another embodiment of the present invention provides a method of screening Mungbean Yellow Mosaic India virus resistant/tolerant plants using the recombinant DNA construct or recombinant vector comprising dimers of MYMIV DNA A and DNA B of Mungbean Yellow Mosaic India Virus (MYMIV) in a single Ti plasmid.

Further the present invention provides a method of screening Mungbean Yellow Mosaic India virus resistant/tolerant plants using the recombinant DNA construct or recombinant vector comprising dimers of MYMIV DNA A and DNA B of Mungbean Yellow Mosaic India Virus (MYMIV) in a single Ti plasmid, wherein the polynucleotide sequence of DNA A is as set forth in SEQ ID NO: 11 and DNA B is as set forth in SEQ ID NO: 12.

In one embodiment, the present invention provides the polynucleotide sequence as set forth in the SEQ ID NO: 11.

In another embodiment, the present invention provides the polynucleotide sequence se set forth n SEQ ID NO: 12.

In yet another embodiment the present invention provides the oligonucleotides having the nucleotide sequence as set forth in SEQ ID NO: 1 to SEQ ID NO: 10.

Surprisingly, it was found that mechanical inoculation of *Agrobacterium* culture comprising the recombinant DNA construct containing dimers of DNA A and DNA B of Mungbean Yellow Mosaic India virus in a single Ti plasmid enhanced the frequency of the virus infection up to 90% to 100% in MYMIV susceptible plants.

The recombinant DNA construct, vectors and the host cells comprising dimers of DNA A and DNA B of Mungbean Yellow Mosaic India Virus (MYMIV) in a single Ti plasmid provided in the present invention are useful as a highly valuable system for infecting the plants with the virus.

The recombinant DNA construct, vectors and the host cells comprising dimers of DNA A and DNA B of Mungbean Yellow Mosaic India Virus (MYMIV) in a single Ti plasmid provided in the present invention are useful for infecting the plants with the virus for screening the virus resistant/tolerant plants from the virus susceptible plants to identify virus resistant plants.

The recombinant DNA construct, vectors and the host cells comprising dimers of DNA A and DNA B of Mungbean Yellow Mosaic India Virus (MYMIV) in a single Ti plasmid provided in the present invention are also useful for tagging MYMIV resistant markers.

Cloning of Full Length MYMIV DNA A

Total DNA from symptomatic leaves of Soybean (*Glycine max*) plant infected with MYMIV was prepared by CTAB method. Other methods known in the art can also be used for isolation of DNA. Full length MYMIV DNA A was amplified by polymerase chain reaction using the primer sequence having nucleotide sequence as set forth in SEQ ID NO: 1 and SEQ ID NO: 2.

```
Afl1: GGATCCATTGTTGAACGACTTTCC    SEQ ID NO: 1

Afl2: GGATCCCACATTGTTAGTGGGTTC    SEQ ID NO: 2
```

Amplified product of 2747 bp obtained was directly cloned into pCR4Blunt-TOPO plasmid vector using (3956 bp) Zero Blunt TOPO PCR Cloning kit (Invitrogen) and the recombinant vector thus obtained was designated as pTOPOA (6703 bp). The recombinant vector pTOPOA was introduced into competent cells DH5α strain of *E. coli*. The methods well known in the art can also be used for cloning the fragment in the suitable cloning vector to obtain the recombinant vector. Transformation of the recombinant vector in *E. coli* or other host cell can be carried out using the methods known in the art. Detailed procedure is provided in Example 1, Construction of Recombinant Vector pTOPOA2 Comprising Tandem Repeat Clone (Dimer) of DNA A Tandem repeats (dimers) of MYMIV DNA A was constructed by further cloning of a full length fragment of DNA A in the original clone-pTOPOA. The recombinant vector thus obtained was designated as pTOPOA' that contains only one active BamHI site. The PstI small fragment, which was obtained from the digestion of the recombinant vector pTOPOA was cloned in the vector pTOPA' at PstI restriction site to obtain full length DNA A. The recombinant vector thus obtained was designated as pTOPOA1 having one BamHI restriction site. The second fragment of BamHI-digested DNA A was cloned in the BamHI site of the pTOPOA1 to obtain the recombinant vector pTOPOA2 comprising the full dimer of DNA A. Please refer to Example 2. Similarly a recombinant vector comprising the DNA A having nucleotide sequence as set forth in SEQ ID NO: 13 was constructed and the recombinant vector was designated as pTOPOC2.

Cloning of Full Length MYMIV DNA B

Total DNA from symptomatic leaves of Soybean (*Glycine max*) plant infected with MYMIV was prepared by CTAB method. Other methods known in the art can also be used for isolation of DNA. Full length MYMIV DNA B was amplified by polymerase chain reaction using the primer sequence having nucleotide sequence as set forth in SEQ ID NO: 3 and SEQ ID NO: 4.

```
Bfl1: CGGGATCCAATGATGCCTCTGGCAATTTGTG SEQ ID NO: 3

Bfl2: CGGGATCCTGGAGATTCAATATCTCAG     SEQ ID NO: 4
```

Amplified product of 2671 bp was directly cloned into pCR4Blunt-TOPO plasmid vector (3956) using Zero Blunt TOPO PCR Cloning kit (Invitrogen). The recombinant vector thus obtained was designated as pTOPOB (6627 bp). Methods well known in the art can also be used for cloning the fragment in the suitable vector. Transformation of the recombinant vector pTOPOB in *E. coli* or other host cell can be carried out by using the methods known in the art. Details are provided in Example 3. Cloning of DNA B was confirmed by restriction digestion and PCR. Full Sequencing of DNA clone was carried out by using the method well known in the art.

Construction of Tandem Repeat Clone (Dimer) of DNA B

Tandem repeats (dimers) of DNA B was constructed by further cloning of a full length fragment of DNA B in the recombinant vector pTOPOB. MYMIV DNA B insert in pTOPOB has two BamHI sites, one at the beginning and another at the end. The recombinant vector thus obtained was designated as pTOPOB2 (9298 bp). Details are provided in Example 4. Similarly a recombinant vector comprising the DNA B having nucleotide sequence as set forth in SEQ ID NO: 13 was constructed and the vector was designated as pTOPOD2.

Construction of Double Dimer by Cloning of Full Tandem Repeats (Dimers) of MYMIV DNA A (A2) and MYMIV DNA B (B2) in pCAMBIA Vector Dimer of MYMIV DNA component B was excised from the recombinant plasmid pTOPOB2 by digestion with EcoRI and was cloned in EcoRI digested T-DNA region of a binary vector pCAMBIA 1305.1 (Cambia, Australia) to make pCAMBIAB2. For cloning of dimer DNA A in the same T-DNA, it was necessary to introduce the restriction sites for SalI and SacI at the two flanking region of DNA A dimer. A PCR reaction was set with primers specific to sequences of TOPO flanking DNA A dimer. The Forward primer with SalI site having nucleotide sequence as set forth in SEQ ID NO: 5 (Cfl1) and reverse primer with SacI at their 5' end having nucleotide sequence as set forth in SEQ ID NO: 6 (Cfl2) were used for the amplification reaction. Detailed procedure is explained in Example 5.

```
                                    SEQ ID NO: 5
Cfl1: GGCGGATCCGTCGACAGCTCAGAATTAACCCTCAC

                                    SEQ ID NO: 6
Cfl2: GGCGGATCCGAGCTGTAGGGCGAATTGAATTTAGC
```

Mobilization of Double Dimer (pCAMBIAA2B2) Clone into *Agrobacterium tumefaciens*

Duplicated tandem repeats of MYMIV DNA A and B in pCAMBIA i.e the plasmid pCAMBIAA2B2 was introduced into *Agrobacterium tumefaciens* strain EHA105 by freeze-thaw method. Other methods such as electoporation can also be used for *Agrobacterium* transformation. Recombinant *Agrobacterium* transformants carrying the full dimer of the DNA A and DNA B was designated as MYMIVA2B2. The transformants were confirmed by PCR and Southern blot analysis for the presence of tandem repeats of DNA A and DNA B. details are provided in Example 6. Other *Agrobacterium* strains well known in the art such as LBA 4404 and EHA 101 can also be used for transformation. Similarly recombinant plant transformation vector pCAMBIAC2D2 was constructed, wherein the vector comprises double dimer of MYMIV DNA A having nucleotide sequence as set forth in SEQ ID NO: 13 and MYMIV DNA B having nucleotide sequence as set forth in SEQ ID NO: 14.

Agroinfection of Plants

Agroinoculation using recombinant *Agrobacterium* cells MYMIVA2B2 comprising pCAMBIAA2B2 plasmid containing the full dimer of DNA A and DNA B was performed by stem inoculation method. Other method known in the art also can be used for agroinfection of plants. For mock inoculation, *Agrobacterium* culture with pCAMBIA vector was used as negative control. Some plants inoculated with YEB+ acetosyringone only and kept in the same condition as 'uninoculated control'. Details are described in Example 7.

Agroinfection of agroinoculated soybean plants was confirmed by polymerase chain reaction using DNA-A and DNA-B specific primers CP1 (SEQ ID NO: 7), CP2 (SEQ ID NO: 8) and BV1 (SEQ ID NO: 9) and BV (SEQ ID NO: 10) (Example 8).

```
CP1: GAAACCTCGGTTTTACCGACTGTATAG   SEQ ID NO: 7

CP2: TTGCATACACAGGATTTGAGGCATGAG   SEQ ID NO: 8

BV: CACCGTCAAGAGGACGTTTACGTCTTC    SEQ ID NO: 9

BV2: AGGCTATGCATGGATATAAATGCATAG   SEQ ID NO: 10
```

Further Southern hybridization was carried out to confirm the integration of the respective viral DNA in agroinfected soybean plants. Southern analysis confirmed integration of various viral DNA forms in Agroinoculated plants with symptoms (Example 9).

To confirm the expression of the transgene ELISA was carried out. Details are provided in Example 10. Protein extracts of the leaves were subjected to ELISA test using polyclonal antibody raised against coat protein. The results corresponded to the PCR and Southern blot results.

EXAMPLES

It should be understood that the following examples described herein are for illustrative purposes only and that various modifications or changes in light will be suggested to persons skilled in the art and are to be included within the spirit and purview of this application acid the scope of the appended claims.

Example 1

PCR Amplification and Cloning of Full Length MYMIV DNA A

Total DNA from symptomatic leaves of Soybean (*Glycine max*) plant was prepared by CTAB method or methods known in the art. Two sets of primers having overlapping region with BamHI site at their 5' ends were designed from published sequence for DNA amplification to amplify full length MYMIV DNA A. The reaction condition was 30 cycles with melting, annealing and polymerizing conditions of 30 sec at 94° C., 1 min at 55° C. and 12 min at 72° C. respectively. The nucleotide sequence of the primers (Afl1 and Afl2) used in the amplification reaction is as set forth in the SEQ ID NO: 1 and SEQ ID NO: 2.

```
Afl1: GGATCCATTGTTGAACGACTTTCC    SEQ ID NO: 1

Afl2: GGATCCCACATTGTTAGTGGGTTC.  SEQ ID NO: 2
```

Amplification reactions were carried out using Pfu polymerase (Stratagene) according to manufacturer instructions. Other polymerase enzymes known in the art also can be used for the amplification of the said DNA figment. Amplified product (2747 bp) was directly cloned into pCR4Blunt-TOPO plasmid vector using (3956 bp) Zero Blunt TOPO PCR Cloning kit (Invitrogen) and the vector was designated as pTOPOA (6703 bp) and introduced into *E. coli* DH56. The methods well known in the art can also be used for cloning the fragment in the suitable cloning vector to obtain the recombinant vector. Transformation of the recombinant vector in *E. coli* or other host cell can be carried out using the methods known in the art.

The recombinant *E. coli* strain DH56 containing the recombinant vector was selected on ampicillin (50 μg/ml), X-gal (40 μg/ml) and IPTG (40 μg/ml) medium. Plasmid DNA was purified by alkaline lysis method using Qiaprep (Qiagen) kit. Methods well known in the art can be use for isolation of the plasmid DNA.

Cloning of DNA A was confirmed by restriction digestion and amplification method. Full Sequencing of DNA clone was carried out by the methods known in the art.

Example 2

Construction of Recombinant Vector pTOPOA2 Comprising Tandem Repeat Clone (Dimer) of DNA A Tandem repeats (dimers) of MYMIV DNA A was constructed by further cloning of a full length fragment of DNA A in the original clone-pTOPOA. MYMIV DNA A insert in recombinant vector pTOPOA has two BamHI sites, one at the beginning and another at the end. For making dimer, one BamHI site was inactivated and other BamHI site was used for the cloning of a BamHI digested second full length DNA A fragment. In brief, PstI digestion of pTOPOA released 1.5 kb (PstI small fragment) and 5.2 Kb (PstI large fragment) fragments. The large fragment was self-ligated. The plasmid thus obtained was designated as pTOPOA' and contains only one active BamHI site. The BamHI site was then inactivated by treating with Klenow fragment of *E. coli* DNA polymerase. The PstI small fragment, which was obtained from the digestion of the recombinant vector pTOPOA was cloned in the vector pTOPA' at PstI restriction site to obtain full length DNA A. The recombinant vector thus obtained was designated as pTOPOA1 having one BamHI restriction site. The second fragment of BamHI-digested DNA A was cloned in the BamHI site of the pTOPOA1 to obtain the recombinant vector pTOPOA2 comprising the full dimer of DNA A. Tandem orientation of DNA A in pTOPOA2 (9450 bp) was checked by restriction analysis.

Example 3

PCR Amplification and Cloning of Full Length MYMIV DNA B

Total DNA from symptomatic leaves of *Glycine max* infected with MYMIV plant was prepared by CTAB method. Two sets of primers having overlapping region with BamHI site at their 5' ends were designed from published sequence for a PCR reaction to amplify full length MYMIV DNA B. The reaction condition was 30 cycles with melting, annealing and polymerizing conditions of 30 sec at 94° C., 1 min at 55° C. and 12 min at 72° C. respectively. The nucleotide sequence of the primes used in PCR reaction is shown in SEQ ID NO: 3 (Bfl1) and SEQ ID NO: 4 (Bfl2).

```
Bfl1: CGGGATCCAATGATGCCTCTGGCAATTTGTG SEQ ID NO: 3

Bfl2: CGGGATCCTGGAGATTCAATATCTCAG.    SEQ ID NO: 4
```

Amplification reactions were carried out by using Pfu polymerase (Stratagene) according to manufacturer instructions. Other polymerase enzymes known in the art also can be used for the amplification of the said DNA figment. Amplified product (2671 bp) was directly cloned into pCR4Blunt-TOPO plasmid vector (3956) using Zero Blunt TOPO PCR Cloning kit (Invitrogen). The recombinant vector thus obtained was designated as pTOPOB (6627 bp). Methods well known in the art can also be used for cloning the fragment in the suitable vector. Transformation of the recombinant vector pTOPOB in *E. coli* or other host cell can be carried out by using the methods known in the art.

The recombinant *E. coli* strain DH5ά comprising pTOPOB was selected on ampicillin (50 μg/ml), X-gal (40 μg/ml) and IPTG (40 μg/ml) medium. Plasmid DNA was purified by alkaline lysis method using Qiaprep kit (Qiagen). Method well known in the art can be use for isolation of the plasmid DNA.

Cloning of DNA B was confirmed by restriction digestion and PCR. Full Sequencing of DNA clone was carried out by using the method well known in the art.

Example 4

Construction of Tandem Repeat Clone (Dimer) of DNA B

Tandem repeats (dimers) of DNA B was constructed by further cloning of a full length fragment of DNA B in the recombinant vector pTOPOB. MYMIV DNA B insert in pTOPOB has two BamHI sites, one at the beginning and another at the end. For making dimer, one BamHI site was inactivated and other BamHI site was used for the cloning of a BamHI digested second full length DNA B fragment. PstI digestion of pTOPOB gave small fragment of 2.4 kb and large fragment of 4.3 kb size. The large fragment was self ligated. The plasmid thus obtained was designated as pTOPOB' and contains only one active BamHI site. The BamHI site was inactivated by treatment with Klenow fragment of *E. coli* DNA polymerase. The PstI small fragment which was obtained from pTOPOB was reinserted at PstI site pTOPOB' to obtain full length DNA B. The recombinant vector thus obtained was designated as pTOPOB1 and contains only one BamHI site. The second fragment of BamHI digested DNA B was cloned in BamHI site of pTOPOB1 to obtain the recombinant vector pTOPOB2 (9298 bp) comprising full dimer of DNA B. Tandem orientation of DNA B in pTOPOB2 was checked by restriction analysis.

Example 5

Construction of Double Dimer by Cloning of Full Tandem Repeats (Dimers) of MYMIV DNA A (A2) and MYMIV DNA B (B2) in pCAMBIA Vector Dimer of MYMIV DNA component B was excised from the recombinant plasmid pTOPOB2 by digestion with EcoRI and was cloned in EcoRI digested T-DNA region of a binary vector pCAMBIA 1305.1 (Cambia, Australia) to make pCAMBIAB2. For cloning of dimer DNA A in the same T-DNA, it was necessary to introduce the restriction sites for SalI and SacI at the two flanking region of DNA A dimer. A PCR reaction was set with primers specific to sequences of TOPO flanking DNA A dimer. The Forward primer with SalI site having nucleotide sequence as set forth in SEQ ID NO: 5 (Cfl1) and reverse primer with SacI at their 5' end having nucleotide sequence as set forth in SEQ ID NO: 6 (Cfl2) were used for the amplification reaction.

```
                                             SEQ ID NO: 5
Cfl1: GGCGGATCCGTCGACAGCTCAGAATTAACCCTCAC

                                             SEQ ID NO: 6
Cfl2: GGCGGATCCGAGCTGTAGGGCGAATTGAATTTAGC
```

Figure 1A:
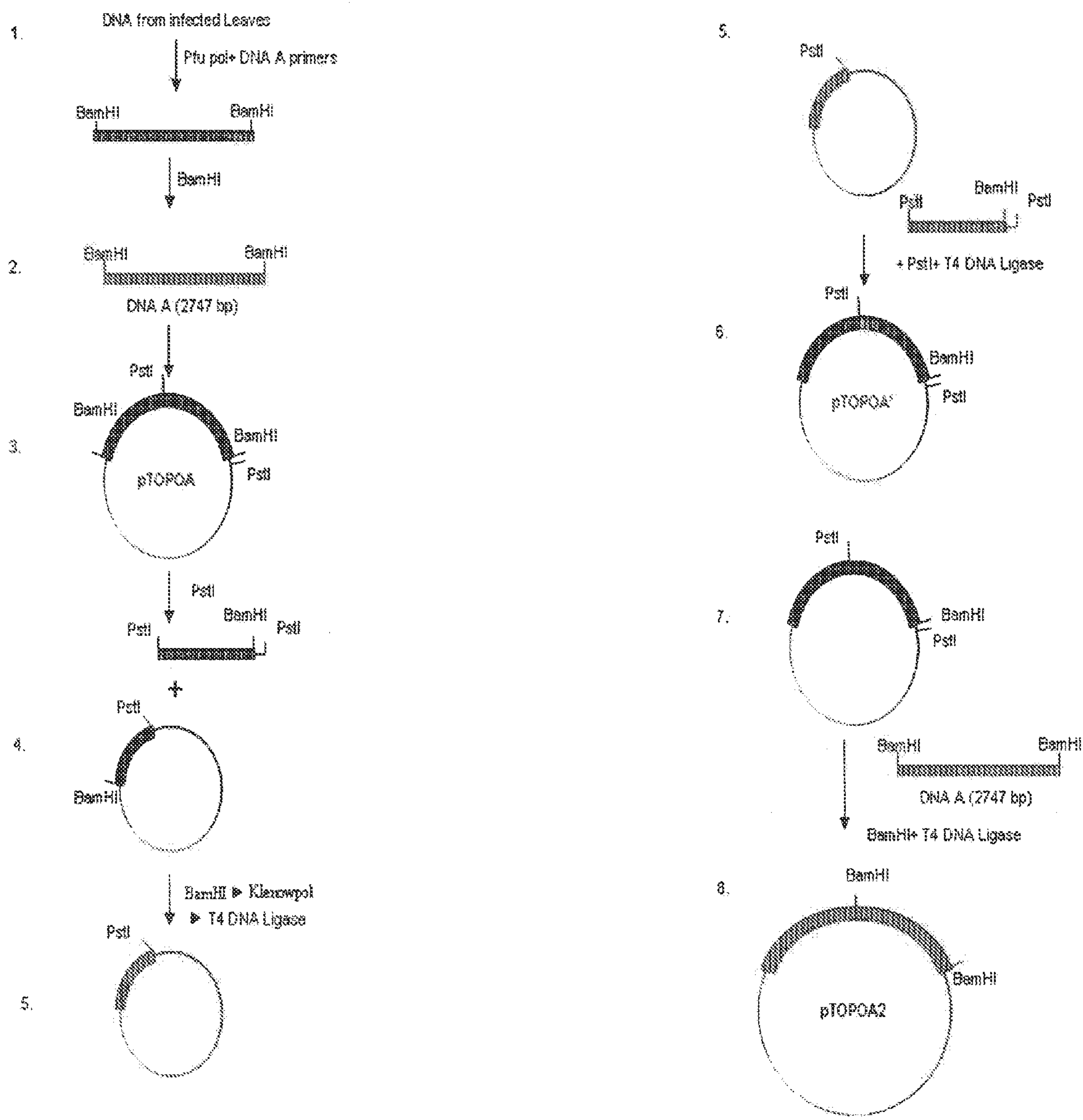
FIG. 1 shows outline showing construction of pCAMBIAA2B2.
Figure 1B:
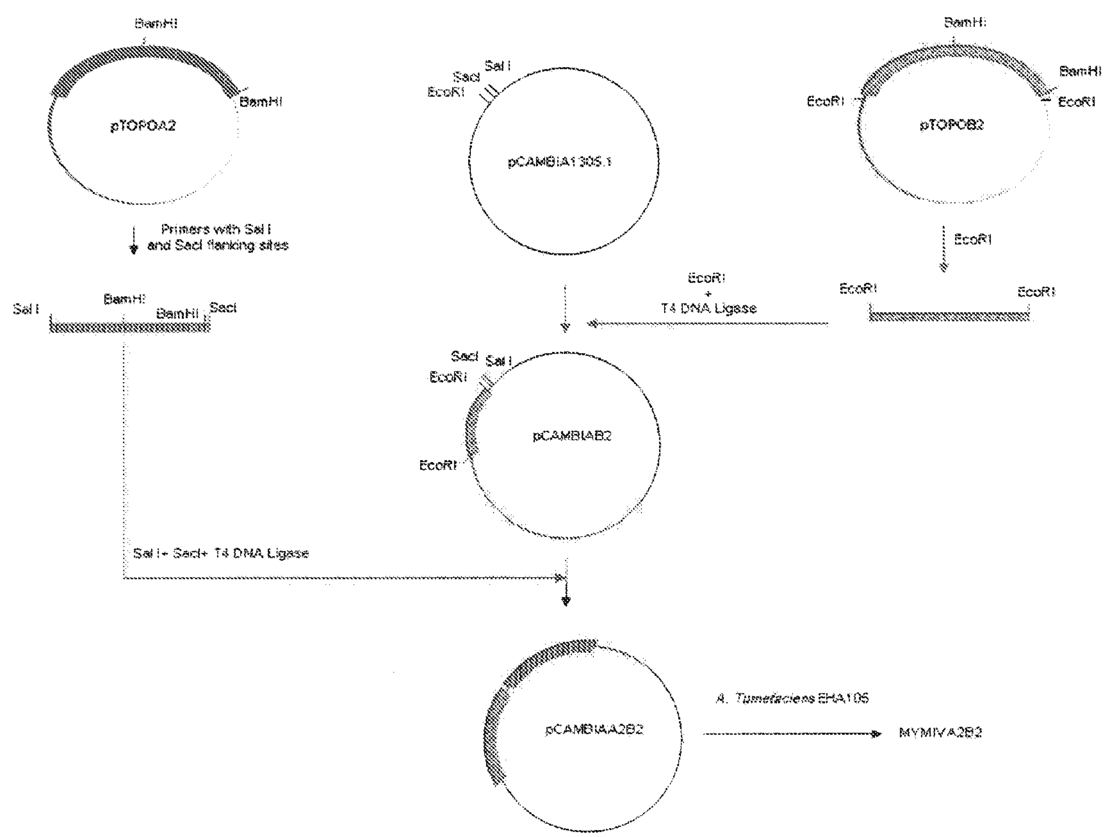

Polymerase chain reaction was carried out with Pfu polymerase. The reaction condition was 30 cycles with melting, annealing and polymerizing conditions of 30 sec at 94° C., 1 min at 55° C. and 15 min at 72° C. respectively. The PCR product was digested by SalI and SacI, and it was cloned in SalI-SacI site in T-DNA of pCAMBIAB2. Resultant clone designated as pCAMBIAA2B2 (22655 bp, FIG. 1) was checked by restriction digestion and it was found that both DNA A and DNA B dimers were on the same T DNA separated by a small stretch of plasmid DNA. The clone was also confirmed by sequencing.

Example 6

Mobilization of Double Dimer (pCAMBIAA2B2) Clone into *Agrobacterium tumefaciens*

Duplicated tandem repeats of MYMIV DNA A and B in pCAMBIA i.e the plasmid pCAMBIAA2B2 was introduced into *Agrobacterium tumefaciens* strain EHA105 by freeze-thaw method. Other methods such as electoporation can also be used for *Agrobacterium* transformation. Plasmid DNA (1-3 μg) was added to 100 μl of competent *Agrobacterium* strain EHA105 in a 1.5 ml centrifuge tube. The tube was freeze in liquid nitrogen for 30 sec. The tube was immediately transferred to 37° C. water bath for 5 min. 1 ml YEB medium (1 g/L yeast extract, 5 g/L beef extract, 5 g/L peptone, 5 g/L sucrose, 2 mM $MgSO_4$) was added to the tubes and kept at 28° C. for 2-3 hrs with gentle shaking. The colonies were selected on YEB-Agar medium supplemented with kanamycine (50 μg/ml). *Agrobacterium* transformants carrying the full dimer of the DNA A and DNA B was designated as MYMIVA2B2. The transformants were confirmed by PCR and Southern blot analysis for the presence of tandem repeats of DNA A and DNA B.

Other *Agrobacterium* strains well known in the art such as LBA 4404 and EHA 101 can also be used for transformation.

Example 7

Agroinfection of Plants

Recombinant *Agrobacterium* cells MYMIVA2B2 comprising pCAMBIAA2B2 plasmid containing the full dimer of DNA A and DNA B were cultured overnight in YEB medium (pH 7.0) at 28° C. The culture was centrifuged at 4000 rpm for 5 min at room temperature. Obtained pellet was resuspended in YEB medium (pH 5.6) with 100 μM Acetosyringone. Soybean seeds were germinated in sterile vermiculite until two leaf stage. Agroinoculation was done by stem inoculation method in which wounds were made around the growing nodal region of the soybean stem by pricking it 5-6 times with 30-gaze needle. About 20 μl of *Agrobacterium* culture (MYMIVA2B2) was put on the wounds. For mock inoculation, *Agrobacterium* culture with pCAMBIA vector was used as negative control. The plants were kept at glass house at 28° C. Some plants inoculated with YEB+acetosyringone only and kept in the same condition as 'uninoculated control'.

Appearance of Symptom of MYMIV-Infection

Six soybean varieties were tested for agroinoculation. Yellow mosaic symptom started to appear on the first leaf above the inoculation point after 10 days of agroinoculation. Within 21 days of inoculation all the newly appeared leaves showed dense yellow mosaic. Mock inoculated and uninoculated plant showed no symptoms. A wild variety UPSM previously known as MYMIV-resistant was used as a positive control that appeared resistant to agroinoculation. The comparative data of infectivity of MYMIV on soybean varieties by agroinoculation with DNA A and DNA B on single plasmid and separate plasmid is provided in Table 1 and 2.

TABLE 1

Infectivity of MYMIV on soybean varieties by agroinoculation with DNA A and DNA B on single plasmid

| S. No. | Soybean variety | No. of agroinoculated plant | No. of plant infected | % (percentage) |
|---|---|---|---|---|
| 1. | JS 335 | 90 | 82 | 91% |
| 2. | JS 71-05 | 10 | 10 | 100% |
| 3. | NRC 37 | 20 | 19 | 95% |
| 4. | TAMS-38 | 20 | 20 | 100% |
| 5. | AMS 353 | 20 | 20 | 100% |
| 6. | AMS 99-24 | 20 | 20 | 100% |
| 7. | UPSM (Wild variety) | 20 | 0 | 0% |

TABLE 2

Infectivity of MYMIV on soybean varieties by agroinoculation with DNA A and DNA B on separate plasmid

| S. No | Soybean variety | No. of agroinoculated plant | No. of plant infected | % (percentage) |
|---|---|---|---|---|
| 1. | JS 335 | 90 | 21 | 23% |
| 2. | JS 71-05 | 10 | 2 | 20% |
| 3. | NRC 37 | 20 | 2 | 10% |
| 4. | TAMS-38 | 20 | 3 | 15% |
| 5. | AMS 353 | 20 | 4 | 20% |
| 6. | AMS 99-24 | 20 | 3 | 15% |
| 7. | UPSM (Wild variety) | 20 | 0 | 0% |

Example 8

DNA Extraction and PCR

Figure 2:
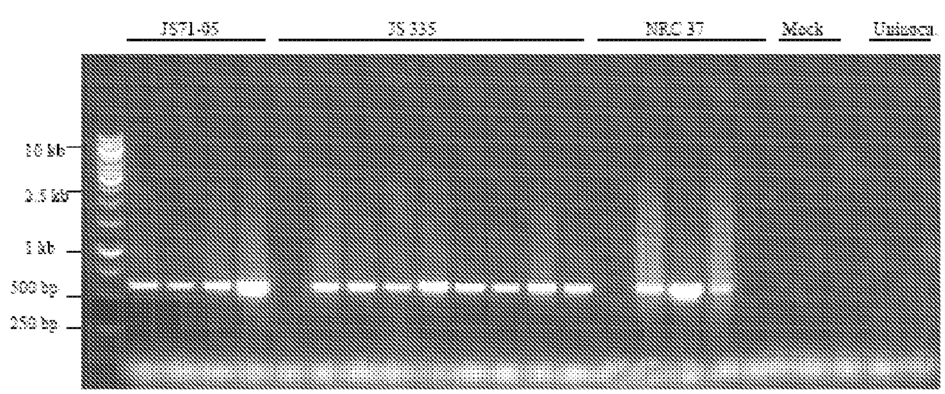
FIG. 2 shows PCR amplification of CP (Coat protein) gene from Agroinoculated soybean plants.

Total DNA was extracted from trifoliate leaves above inoculation point by CTAB method. For checking the presence of viral DNA by polymerase chain reaction (PCR), both DNA-A and DNA-B specific primers CP1, CP2 and BV1 and BV were used. The primers CP1 and CP2 having nucleotide sequence as set forth in SEQ ID NO: 7 and SEQ ID NO: 8 correspond to coat protein gene of DNA-A whereas primers BV1 and BV2 having nucleotide sequence as set forth in SEQ ID NO: 9 and SEQ ID NO: 10 corresponds to movement protein gene of DNA-B. After PCR reaction, bands of 575 bp, which correspond to coat protein gene and 652 base pair, which correspond to movement protein gene, were obtained from agroinoculated plants. No PCR fragments were obtained from mock inoculated, uninoculated or resistant plant (FIG. 2).

```
CP1: GAAACCTCGGTTTTACCGACTGTATAG   SEQ ID NO: 7

CP2: TTGCATACACAGGATTTGAGGCATGAG   SEQ ID NO: 8

BV: CACCGTCAAGAGGACGTTTACGTCTTC    SEQ ID NO: 9

BV2: AGGCTATGCATGGATATAAATGCATAG   SEQ ID NO: 10
```

Example 9

Southern Hybridization

Southern hybridization was carried out to confirm the integration of the respective viral DNA in plants. About one μg of total DNA was electrophoresed on 1% agarose gel in tris-acetate buffer transferred to nitrocellulose membrane and hybridized with $\acute{\alpha}^{32}$P labeled probe made by a PCR fragment of MYMIV coat protein gene and movement protein gene. Radiolabeled probes were produced by random primer labeling method or methods known in the art. Southern hybridization was carried out using the methods well known in the art. Southern analysis confirmed integration of various viral DNA forms in Agroinoculated plants with symptoms. No corresponding bands were found in uninoculated and mock-inoculated plants and the plants with no symptoms (FIG. 3).

Example 10

Detection by ELISA

Antibody-sandwich ELISA was used to detect MYMIV coat protein from infected soybean plants. Polyclonal antibody was raised against coat protein of MYMIV. This antibody was used to prepare capture antibody by diluting it to coating buffer (0.1M $NaHCO_3$ Ph 8.6). Each well of ELISA micro titer plate was coated by adding 50 μl of coating buffer and incubating over night at 4° C. Next day wells were washed with deionized water and blocked with 50 μl of 3% BSA/PBS at room temperature. After 1 h blocking solution was shacked off and protein extracts from infected leaves were added into the wells. The plate was incubated at 37° C. for 1 h. After this protein extracts was shacked off from the wells and washed with 10× PBS/Tween 20 (0.05%). Now 25 μl of secondary antibody-alkaline phosphatase enzyme conjugate was added per well at 1:1000 dilution in 1% BSA/PBS. Plate was incubated at 37° C. for 1 h. After 1 h wells were washed with 10×PBS/Tween 20 (0.05%). Substrate solution was added to each well and plate was developed at 37° C. for 30 minutes.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A recombinant DNA construct comprising dimers of DNA A and DNA B of Mungbean Yellow Mosaic India Virus (MYMIV) in a single Ti plasmid, wherein the polynucleotide sequence of DNA A is 99% identical to the nucleotide sequence as set forth in SEQ ID NO: 13 and the polynucleotide sequence of DNA B is 97% identical to the nucleotide sequence as set forth in SEQ ID NO: 14.

2. A recombinant DNA construct comprising dimers of MYMIV DNA A and DNA B of Mungbean Yellow Mosaic India Virus (MYMIV) in a single Ti plasmid, wherein the polynucleotide sequence of DNA A is as set forth in SEQ ID NO: 11 or SEQ ID NO: 13 and the polynucleotide sequence of DNA B is as set forth in SEQ ID NO: 12 or SEQ ID NO: 14.

3. A recombinant host cell comprising the recombinant DNA construct as claimed in claim 1 or 2, wherein the host cell is selected from a group consisting of *E. coli, Agrobacterium* and plant cell.

4. A method of screening Mungbean Yellow Mosaic India virus resistant/tolerant plants, comprising agroinoculating plants with *Agrobacterium* cells comprising a recombinant DNA construct of claim 1 or claim 2, and observing the presence or absence of MYMIV symptoms.

5. The method as claimed in claim 4, wherein said recombinant DNA construct comprises the polynucleotide having nucleotide sequence as set forth in SEQ ID NO: 11 and SEQ ID NO: 12.

6. An isolated polynucleotide having nucleotide sequence as set forth in SEQ ID NO: 11.

7. An isolated polynucleotide having nucleotide sequence as set forth in SEQ ID NO: 12.

8. A set of oligonucleotides consisting of (a) SEQ ID NO: 1 to SEQ ID NO: 4, or (b) SEQ ID NO: 5 and SEQ ID NO: 6.

9. The method as claimed in claim 4, wherein said explant is selected from the group consisting of a seed, a seedling and an embryo.

* * * * *

SEQUENCE LISTING

<160> NUMBER OF SEQ ID NOS: 14

<210> SEQ ID NO 1
<211> LENGTH: 24
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 1
ggatccattg ttgaacgact ttcc 24

<210> SEQ ID NO 2
<211> LENGTH: 24
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 2
ggatcccaca ttgttagtgg gttc 24

<210> SEQ ID NO 3
<211> LENGTH: 31
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 3
cgggatccaa tgatgcctct ggcaatttgt g 31

<210> SEQ ID NO 4
<211> LENGTH: 27
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 4
cgggatcctg gagattcaat atctcag 27

<210> SEQ ID NO 5
<211> LENGTH: 35
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 5
ggcggatccg tcgacagctc agaattaacc ctcac 35

<210> SEQ ID NO 6
<211> LENGTH: 35
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 6
ggcggatccg agctgtaggg cgaattgaat ttagc 35

<210> SEQ ID NO 7
<211> LENGTH: 27
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 7
gaaacctcgg ttttaccgac tgtatag 27

<210> SEQ ID NO 8
<211> LENGTH: 27
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 8
ttgcatacac aggatttgag gcatgag 27

<210> SEQ ID NO 9
<211> LENGTH: 27
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 9
caccgtcaag aggacgttta cgtcttc 27

<210> SEQ ID NO 10
<211> LENGTH: 27
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 10
aggctatgca tggatataaa tgcatag 27

<210> SEQ ID NO 11
<211> LENGTH: 2739
<212> TYPE: DNA
<213> ORGANISM: MUNGBEAN YELLOW MOSAIC INDIA VIRUS (MYMIV)

<400> SEQUENCE: 11
acctgagtgc cccgcgaccg gtgtattggg gttgctttag cttttctgct ttttgggtac 60
ccttatcttt agtcgttcaa tcagaagcgc tcctcagcgc tatgttaatt caaatttgaa 120
ttataaagca gatgcacact ctgaacccac taacaatgtg ggatccattg ttgaacgact 180
ttcccaaatc agtgcatgga ttccggtgca tgttggcaat aaagtatttg cagcaagttc 240
aagagaatta tcctactaat tctgttggtt attcgtacct tacagggtta attcaggtat 300
tgcgcatccg gaatcatgcc aaagcggacc ttcgatactg ccttctctac cccgatatcg 360
aatgcacgga ggagattgaa cttcgatacc ccgctcatgc tccatgcttc tgcgggaggt 420
gtccctacca acatgaaaag aaggcgttgg accaaccgcc ccatgtggag gaaacctcgg 480
ttttaccgac tgtataggtc ccctgatgtc cctcgtggtt gtgagggacc atgtaaagtt 540
caatcatttg agcagaggca tgatattgcc cacacaggca aagtgatttg catatcggac 600
gtgactcgag gtaatggaat tacacatcgt attggcaaac gtttttgcat caagtccgtg 660
tacattactg ggaaggtttg gatggacgaa aacattaagt ccaaaaatca cacaaacact 720
gtgatgttca agttatgtcg tgacagacga ccatttggta cacccatgga ttttggtcaa 780

```
gtttttaaca tgtatgacaa cgagccaagt acagctactg tgaaaaacga tctgcgtgat    840
cgttatcaag tcttgcgaaa gtttaatgcc actgttactg gtggccaata tgcttgtaag    900
gaacaagcga tggtgaatcg ttttttcaaa gttaataatt atgttgttta caaccaccaa    960
gaggcagcga agtatgagaa ccatactgag aacgcattat tattgtatat ggcatgtact   1020
catgcctcaa atcctgtgta cgcaacactt aaaattcgga tctattttta cgattcgata   1080
ttgaattaat aaagtttgta ttgaacatta tgcgtaaagc ttacatcctc caccaggtgg   1140
agtttattgt acaagaaatc cgacgcgaaa tataaaatat ttgctaagct aatgacccct   1200
aaattattta gaaacctaaa taattggtta cggaagatcg ataagatcat cccagaagtc   1260
gccgtcaaat agtggaagag cttcaagtcc aggaagcact tgtgcatccc cagtgctttc   1320
ttcaacctgt ggttgaacat tatgcgcagc ttggtcacca tcattctgga ccctgctcga   1380
attggactgt ggtgcatgat cctgaaagag aggggatttt gcacctccca gatatagacg   1440
ccactcctga gttgagctgc agtgatgtac tcccctgtgc gaaaagccat agttacggca   1500
gttgatatgg atgtaatagc tacacccaca ggttagatca attcgagagc gtcgaattgc   1560
tctcttcttg gcgaccctgt gttgaacctt gattgacgga ggagaacagt ggttctttga   1620
gggtgtagaa ctccgcattc tttgaagccc actgtttaag cgcagcattg ttctcttcat   1680
ccaagtactc tttataggag gacttgggac cagcgttaca cagaaagatg gtggggatac   1740
cacctttaat tttagtgggc ttcccgtact tgacgttaga ctgccagtct ctttgcgcgc   1800
ccatgaattc tttgaaatgt ttcaaataat gtggatcaac gtcatcaatg acgttgtacc   1860
atgcctcgtt agagtatgtt ttgtcgttta gatccaaatg gccgcaaaga taattatgag   1920
gacctatggc acgtgcccac atggttttac ccgtgcgact atctccttca ataacaatac   1980
taataggtct gtctggccgc gcagcgggat ctctcacatt tctttcagcc catgaagaaa   2040
tgtagcttgg aaccttgtcg aatgactcca atgtaaaagg cgactcatat gcctgtgtag   2100
gctctgtgaa tatccgagac aaattacaat ttaaattatg aaattgtaaa ataaaatcct   2160
ttggggcctt ttcctttaat ataaggaggg cctccaactt tgatccagag ttgagtgcct   2220
cggcgtatgc gtcgttggca gattgtttac ctcctcgagc tgatcggcca tcgatttgga   2280
aggttccatg atcaagaatg tctccgtctt tctccatgta tgttttaaca tctgagcagc   2340
ttttagctgc ctgaatgttc ggatggtaat gtgttgacct gcatctggaa tggaggtcga   2400
agaacctttg gttcctcgtt tggtgcttcc cttcgaactg aagcagaaca tggagatgag   2460
gctgtccatc ttcatggagt tcacgacaga tgcggatgaa tttcttgtta acaggtgttg   2520
acaaggctag tagttgttca agagcgtcct cctttgtaag aggacatttg ggatatgtca   2580
agaaatagtt ttttgcgttt atagcaaaac gaccatccct tggcattttt aaagtcgttt   2640
tggtatcggt gtacaccgat tgccttctct agccccctat cggtgtatcg gtgtactata   2700
tatactagag ctactaaaag cctctagggg cactcagct                          2739
```

```
<210> SEQ ID NO 12
<211> LENGTH: 2671
<212> TYPE: DNA
<213> ORGANISM: MUNGBEAN YELLOW MOSAIC INDIA VIRUS (MYMIV)

<400> SEQUENCE: 12

acctgagagc cccgcgaccg gtgtatcggt tttagagcac gtgggtggtc cctctattac     60
gtggcgcact ctggagtctc gctcgatgct agtttaatga acgactactt agaattacag    120
gtaaccggat aggtgaccgt tcgtacatgg acaaattcgt cttttcctca aaaagaccgt    180
```

-continued

```
ttttgccatt cggtgtacaa cttttaatgc ctaaggccgc gaaacccttg gggtatttat    240
gtcatttcat atgaaatgac tttaatttga aatcgttttt ctataaaacg atcttcgtcc    300
aatttgtcca tactatgcta tacgcacaat gtcgttcatt tatttttatt taatcttttc    360
aatatcttca tctatatata aatgaaaaca tgaacgtgag ttttcaacca tgaaatgttt    420
aaccggaatt atcgcacccc ttttaaatta cgccatagta attttggtta tagatggcag    480
cctatgaccc cgtcaagagg acgtttacgt cttaataagc ctagtgcttc acgtaaattg    540
tcatatgacc gcgtggaacg ggaaatgcgt acaaattcca ttgttgaggt tcaacatgga    600
agccatatgt cccttgagaa gaatacggat gtatcttcat ttgtgcaata ccctgttcgt    660
ggaatcaacg gtgacggacg ttgtagggat tacatcaagt tacttaaact tgatgtctct    720
ggtgtgataa acattaagtc ttcgaatgga gaccaaagca tggaaccagg tgacaggtta    780
agtggcctat ttatcctgac tgtcttgcta gacaagaaac cctatcttcc agaaggtgtg    840
aataagttac cctcctttgc ggagttattt ggaccttatt ctgctgcata tgcgaatatc    900
cacctcttgg attctcaaaa gccacgcttc aaggtccttg ggacaataaa gaagtttgtg    960
aactgcacac caggaacatt atatggccct ttgaaattaa atatgccgtt gtcccggcga   1020
aagtgtcctt tgtggactac gttcaaggac cctgatcagg gtaattgtgg tggaaattat   1080
aagaatattt ccaaaaatgc tattgtattg agctatgcat ttatatcaat gcatagccta   1140
attgtggaac catattttca atttgaattg aaatacgttg gataaaataa ataaagattt   1200
atttatttta actatgttac aactgtttgt tcacattaga acgttgactt atgagacatt   1260
tgctaatagt cgtctctata atgtcctcta tttctctttt gctcattgtg ttggattggg   1320
tctgagatat tgaatctcca ggatccaatg atgcctctgg caatttgtgc aaatgtttaa   1380
gtgggtaatc tgcgtccgaa gtgctcgtgt tgtctagaat attgggcctg tcgttacttg   1440
tgtatcgcat ggaactgctc cgtccaatag atgaccttgt agcccaagtt tcacctggct   1500
gtagcataat gggcctatgg ccagtatttg gatatggacc ctgattgggt cctggattaa   1560
gcaaacgcct aatgggcttg ggcttctcaa cagaccaaaa gtccacacag tctgcagtgt   1620
agtccttaga caatatgttt attgtcgggg gtttaaacct tatgtctgtt gagtgttttg   1680
cggaagacaa tttcaatttg gcctttatct gggcaaatgt tgttccgtcg atcacgttgg   1740
agtcttcgac cttgtagact atctcccatg gtgtttcatc ctttagagag aagaaggatg   1800
atgagaaata atggagatcg acgttacatg caattgggaa ggtgaaggca gcttgtgctg   1860
cttgttcata gcttagcctt gtgtcacgaa ttgtgacaat gaccgttccc ttagcattga   1920
acggaacttg gtttctgtat tcgatcacag catgatcgac cttcatgcat ctgcccatta   1980
tctggacggt cttctgttcc agataagatg gaaattgtaa ctttatgggc atctcgttgt   2040
tggtcagtct gtattcgcaa ctctttgtct ccacatattt attattaacg actgctcctg   2100
aataattctc cattattcag aacttgtgtt gcgaattaat ccctgcaaag tttgacaaac   2160
caggaaatta tactattaat ttctaatagg ccgcgccagc ggcaatgaga agagtttata   2220
attataatca taatttaaac caaacaggga aaaagacatt taatacctga ttgtgggtat   2280
caatcccaga aaacacaagc acttgatgtg tacagaggaa gtaacaaata ttttattaaa   2340
tatttgttgt tttgatatat gtgattgatt ctatcaatcg atttaaataa aggtgaaaca   2400
tgcgcaggat tgggtcctgg atattaaata ggggattatt taatatcccc aaatggacat   2460
atctggttcc tccagcgttt cggtgtctaa gcgcttgttt ctagagcgag aaacttgatt   2520
ctagagagag aagcatagca aaacgcaaaa tgctaggcaa aagagcgtgt cgtttcgatt   2580
```

cggtgtacac cgattgcctt ctctagcccc ctatcggtgt attggtgtac tatatatagt 2640
aaagttacta ggggctctca gatataatat t 2671

<210> SEQ ID NO 13
<211> LENGTH: 2739
<212> TYPE: DNA
<213> ORGANISM: MUNGBEAN YELLOW MOSAIC VIRUS (MYMIV)

<400> SEQUENCE: 13
acctgagtgc cccgcgaccg gtgtattggg gttgctttat cttttttgct ttttgggtac 60
ccttatcttt agtcgttcaa tcagaagcgc tcctcagcgc tatgttaatt caaatttgaa 120
ttataaagca tgtgcacact ctgaacccac taacaatgtg ggatccattg ttgaacgact 180
ttcccaaatc agtgcatgga ttccggtgca tgttggcaat aaagtatttg cagcaagttc 240
aagagaatta tccttctaat actgttggtt attcgtacct tacagggtta attcaggtat 300
tgcgcatccg gaatcatgcc aaagcggacc tacgatactg ccttctctac cccgatatcg 360
aatgcacgga ggagattgaa cttcgatacc ccgctcatgc tccctgcctc tgcgggaggt 420
gtccctacca acatgaaaag aaggcgttgg accaaccgcc ccatgtggag gaaacctcgg 480
ttttaccgac tgtataggtc ccctgatgtc cctcgtggtt gtgaggggcc atgtaaagtc 540
caatcatttg agcagaggca tgatattgcc cacacaggca aagtgatttg catatcggac 600
gtgactagag gtaatggaat tacacatcgt attggcaaac gtttttgcat caagtccgtg 660
tacattactg ggaaggtttg gatggacgaa aacattaagt ccaaaaatca cacgaacact 720
gtgatgttca agttatgtcg tgacagacga ccatttggta cacccatgga ttttggtcaa 780
gtttttaaca tgtatgacaa cgagccaagt acagctactg tgaagaacga tctgcgtgat 840
cgttatcaag tcttgcgaaa gtttaatgcc actgttactg gtggccaata tgcttgtaag 900
gaacaagcca tggtgaatcg ttttttcaaa gttaataatt atgttgttta caaccaccag 960
gaggcagcga agtatgagaa ccatactgag aacgcattat tattgtatat ggcatgtact 1020
catgcctcaa atcctgtgta tgcaacactt aaaattcgga tctattttta cgattcgata 1080
ttgaattaat aaagtttgta ttgaacatta tgcgtaaagc ttacatcctc caccaggtgg 1140
agtttattgt acaagaaatc cgacgcgaaa tataaaatat ttgctaagct aatgacccct 1200
aaattattta gaaacctaaa taattggtta cggaagatcg ataagatcat cccagaagtc 1260
gccgtcaaat agtggaagag cttcaagtcc aggaagcact tgtgcatccc cagtgctttc 1320
ttcaacctgt ggttgaacat tatgcgcagc ttggtcacca tcattctgga ccctgctcga 1380
attggacggt ggtgcatgat cctgaaagag aggggatttt gcacctccca gatatagacg 1440
ccactcctga gttgagctgc agtgatgtac tcccctgtgc gaaaatccat agttacggca 1500
gttgatatgg atgtaatagc tacacccaca ggttagatca attcgagagc gtcgaattgc 1560
tctcttcttg gcgaccctgt gttgaacctt gattgacgga ggagaacagt ggttctttga 1620
gggtgtagaa ctccgcattc tttgaagccc actgtttaag cgcagcattg ttctcttcat 1680
ccaagtactc tttataggag gacttgggac cagcgttaca cagaaagatg gtggggatac 1740
cacctttaat tttagtgggc ttcccgtact tgacgttaga ctgccagtct ctttgcgcgc 1800
ccatgaattc tttgaaatgt ttcaaataat gtggatcaac gtcatcaatg acgttgtacc 1860
gtgcctcgtt agagtatgtt ttgtcgttta gatccaaatg gccgcaaaga taattatgag 1920
gacctatggc acgtgcccac atggttttac ccgtgcgact atctccttca ataacaatac 1980
taataggtct gtctggccgc gcagcgggat ctctcacatt tctttcagcc catgaagaaa 2040
tgtagcttgg aaccttgtcg aatgactcca atgtaaaagg cgactcatat gcctgtgtag 2100
gctctgtgaa tatgcgagac aaattacaat ttaaattatg aaattgtaaa ataaaatcct 2160
ttggagcctt ttcctttaat ataaggaggg cctccaactt tgatccagag ttgagtgcct 2220
cagcgtatgc gtcgttggca gattgtttac ctcctcgagc tgatcggcca tcgatttgga 2280
aggttccatg atcaagaatg cctccgtctt tctccatgta tgttttaaca tctgagcagc 2340
ttttagctgc ctgaatgttc ggatggtaat gtgttgacct gcatctggaa tggaggtcga 2400
agaacctttg gttcctcgtt tggtgcttcc cttcgaactg aagcagaaca tggagatgag 2460
gctgtccatc ttcatggagt tcacgacaga tgcggatgaa tttcttctta acaggtgttg 2520
acaaggctag tagttgttca agagcgtcct cctttgtaag aggacatttg ggatatgtca 2580
agaaatagtt ttttgcgtta atagcaaaac gaccatccct tggcattttt aaagtcgttt 2640
tggtatcggt gtacaccgat tgccttctct agccccctat cggtgtatcg gtgtactata 2700
tatactagag ctactaaaag cctctagggg cactcagct 2739

<210> SEQ ID NO 14
<211> LENGTH: 2669
<212> TYPE: DNA
<213> ORGANISM: MUNGBEAN YELLOW MOSAIC VIRUS (MYMIV)

<400> SEQUENCE: 14
acctgagagc cccgcgaccg gtgtatcggt tttagagcac gtgggtggtc cctctattac 60
gtggcgcact ctggagtctc gctcgaagct tgtttattga acgactactt agaattacag 120
gtaaccggat aggtgaccgt tcgtacatgg acaaattggt cttttcctca aaaagaccgt 180
ttttgccatt cggtgtacaa gctttaatgc ctaaggccgc gaaacccttg ggtatttat 240 gtcatttcat tggaaatgac tttaatttga aatcgttttt ctataaaacg atcttcgtcc 300
aatttgtcca tactatgcta tacgcacaat gtcgttcatt tatttttatt taaacttttc 360
aatatcttca tctatatata aatgaagaca tgaacgtgag ttttcaacca tgaaatgttt 420
aaccggaatt atcgcacccc ttttaaatta cgccatagta atttggttta tagatggcag 480
cctatgaccc cgtcaagagg acgtttacgt cttaataagc ctagtgcctc acgtaaatta 540
tcatatgacc gcgtggaacg ggaaatgcgt acaaattcca ttgttgaggt tcaacatgga 600
agccatatgt cccttgagaa gaatacggat gtatcttcat ttgtgcaata ccctgttcgt 660
ggaatcaacg gtgacggacg ttgtagggat tacatcaagt tacttaaact tgatgtctct 720
ggtgtgataa acattaagtc ttcgaatgga gaccaaagca tggaaccagg tgacaggtta 780
agtggcctat ttattctgac tgtcttgcta gacaagaaac cctaccttcc agaaggtgtg 840
aataagttac cgtcatttgc ggagttattt ggaccttatt ctgctgcata tgcgaatata 900
cacctcttgg attctcagaa gccccgcttc aaagtccttg ggacaataaa gaagtttgtg 960
aactgcacat cagggacaat atatggccct ttgaaattaa atatgccgtt gtcccggcga 1020
aagtgtcctt tgtggactac gttcaaggac cctgatcagg gtaattgtgg tggaaattat 1080
aagaatattt ccaaaaatgc tattgtattg agctatgcat ttatatcaat gcatagccta 1140
attgtggaac catattttca atttgaattg aaatacgttg gataaaataa ataaagattt 1200
atttattttc actatgttac aactgtttgt tcacatcaga acgttgactt atgagacatt 1260
tgctaatagt cgtctctata atgtcctcta tttctctttt gctcattgcg ttggattggg 1320
tctgagatat tgaatctcca ggatccaatg atgcctctgg cgatttgtgc aaatgtctaa 1380
gtgggtaatc tgcgtccgaa gtgctcgtgt tgtctagaat attaggcctg tcgttacttg 1440

-continued

```
tgtatcgcat ggaactgctc cgtccaatag atgaccttgt agcccaagtc tcacctggct   1500

gtagcataat gggcctatgg ccagtatttg gatatggacc ctgattgggt cctggattaa   1560

gcaaacgcct aatgggcttg ggcttctcaa cagaccaaaa gtccacacag tctgcagtgt   1620

agtctttaga caatatgttt attgtcgggg gtttaaacct tatgtctgtt gagtgttttg   1680

cggaagacaa tttcagtttg gcctttatct gggcaaatgt tgttccgtcg atcacgtttg   1740

agtcttcaac cttgtacact atctcccatg gtgtttcatc ctttagagag aagaaggatg   1800

acgagaaata atggagatcg acgttacatg caattgggaa ggtgaaagca gcttgtgctg   1860

cttgttcata gcttagcctt gtgtcacgaa ttgtgactat gaccgttccc ttggcattga   1920

acggaacttg gtttctgtac tcgatcacag catgatcgac cttcatgcat ctgcccataa   1980

tctggacggt cttctgttcc agataagatg gaaattgtaa cttgatgggc atctcgttgt   2040

tgctcagtct gtattcgcaa ctctttgtct ccacatattt attattaacg actgctcctg   2100

aataattctc cattattcag aaattgtgtt gcgaattaat ccctgaaaag gaatacacac   2160

ccggaaatta ttctaataat ttcaattagg ccgcgcagcg gcaatgaggg tagtttatat   2220

ttaaaatcat aatctaaacc aaacagggaa aaagacattt aatacctgat tgtgggtatc   2280

aatcccagaa aacacaagca cttgatgtgc acagaggaag taacaaatat tttattaaat   2340

atttgttgtt gtgataattg tgattgattc tatcaatcga tttaaataat tgtgagacat   2400

gcgcaggatt gggtcctgga tattaaatag gggattattt aatatcccta aatggacata   2460

tctggtgcct ccagcgtttc ggtgtctaag cgcatgtttc tagagcgaga aacttgtttc   2520

tagagagaga tgcttagcaa aacgcaaaat gctaggcaaa agagcgtgtc gtttcgaatc   2580

ggtgtacacc gattcattct ctagccccct atcggtgtat tggtgtacta tatatagtaa   2640

agttactagg ggctctcaga tataatatt                                     2669
```